(12) United States Patent
Levy (10) Patent No.: US 8,647,255 B2
(45) Date of Patent: Feb. 11, 2014

(54) SEXUAL STIMULATION DEVICES AND METHODS

(75) Inventor: David Levy, Berkeley, CA (US)

(73) Assignee: Tricatalyst, LLC, Berkeley, CA (US)

( * ) Notice: Subject to any disclaimer, the term of this patent is extended or adjusted under 35 U.S.C. 154(b) by 1176 days.

(21) Appl. No.: 12/539,529

(22) Filed: Aug. 11, 2009

(65) Prior Publication Data

US 2010/0041944 A1 Feb. 18, 2010

Related U.S. Application Data

(60) Provisional application No. 61/087,821, filed on Aug. 11, 2008.

(51) Int. Cl.
*A61F 5/00* (2006.01)

(52) U.S. Cl.
USPC .......................................................... 600/38

(58) Field of Classification Search
USPC .............. 600/38–41; 601/121, 122, 132, 134, 601/148, 149, 151–153
See application file for complete search history.

(56) References Cited

U.S. PATENT DOCUMENTS

| 5,782,818 | A |   | 7/1998 | Shubin |          |
|-----------|---|---|--------|--------|----------|
| 5,806,523 | A | * | 9/1998 | Shubin, Sr. | 128/842 |
| 5,807,360 | A |   | 9/1998 | Shubin |          |
| 6,039,703 | A | * | 3/2000 | Badilla | 601/61 |
| 6,423,017 | B2 | * | 7/2002 | Brotz | 601/151 |
| 7,104,950 | B2 |   | 9/2006 | Levy |          |
| 7,238,163 | B1 | * | 7/2007 | Fried et al. | 601/122 |

* cited by examiner

*Primary Examiner* — Samuel Gilbert (57) ABSTRACT

Sexual stimulation devices and methods that provide highly varied and dynamically controllable sensations, both directly under manual control of the user and indirect electronic control, and in such a way as to provide sensations to specific regions of the sexual organs.

28 Claims, 5 Drawing Sheets

SEXUAL STIMULATION DEVICES AND METHODS

CROSS-REFERENCE TO RELATED APPLICATION

This application claims the benefit of the Aug. 11, 2008 filing date of provisional application 61/087,821, of the same title. This prior application is incorporated herein by reference in its entirety.

TECHNICAL FIELD

This disclosure relates to devices and methods to sexually stimulate the human body.

BACKGROUND

The prior art is replete with sexual devices that provide a suction to a penis or vibration to a penis. Both provide sensations that are diffuse and distributed over the length of the shaft in a consistent and unchanging manner. Except for amplitude, the character of the output does not change. Existing vacuum devices, for example, apply a fairly consistent stimulus along the length of the penis and vibratory devices provide a stimulus that emanates from the specific location at which the vibrator motor is disposed. In both cases the amplitude of the sensation can be modified, however the stimulus remains in the same place with respect to the device and therefore provides a relatively unchanging stimulus. The device must be moved relative to the person to create a changing sensation. Furthermore the character and range of sensations provided by existing devices are limited, and moreover the degree of dynamic and interactive control that may be imposed by the user is also limited. The sensations provide "gross" sensations, rather than focused, customized, or sensations limited within a region.

It is therefore desirable to provide stimuli that can change during a usage, not just in amplitude or frequency but in character and/or shape. It is desirable to provide devices capable of providing stimuli that are varied, controllable, and subtle. It is further desirable to have the variable sensation independent of any thrusting motion. It is further desirable to have the variable sensation dependent on the thrusting motion in a variety of predictable and semi-predictable and non-predictable ways. It is also desirable to have the sensation dynamically variable, and yet still further, under dynamic control, whether the user is co-located, or distant. It is yet further desirable to have the same sensations provided at different locations within the device at different times. It is yet further desirable to couple the above benefits to a sensed level of arousal. It is further desirable to provide an artificial vagina that provides a contractile output. It is yet further desirable to provide the stimulus of an undulating contractile output. It is also desirable to allow a device to provide a localized output sensation at a different location at which the control is input.

It is further desirable to provide this functionality concurrent with and integral to the action of grasping the device.

DESCRIPTION OF DRAWINGS

Like reference symbols in the various drawings indicate like elements.

DETAILED DESCRIPTION

Figure 1:
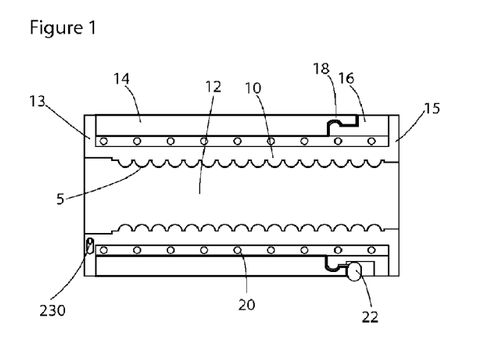
FIG. 1 is an axial sectional view of a male stimulation device with rotary sense variation.

FIG. 1 shows an embodiment in which sleeve 10 manufactured of low durometer elastomeric material, such as styrene-ethylene propylene-styrene block copolymer (SEPS) or any material that approximates human flesh and molded to include cavity 12 designed to accommodate a human penis. It is known in the art that a suitable elastomeric gel may be formed from a mixture of plasticizing oil and a block copolymer comprising an admixture of a styrene ethylene butylene styrene block copolymer and a styrene ethylene propylene styrene block copolymer. A ratio of about 1:1 is desirable, but the two may be combined in ratios in the range from about 1:4 to 4:1. The contact surface 5 of cavity 12 may be smooth or have a texture as shown. A first end 13 of sleeve 10 is constrained by a first housing element 14. A second end 15 of sleeve 10 is constrained by a second housing element 16. Housing element 14 and second housing element 16 are rotatably engaged by rotary element 18. Rotation of housing elements 14 and 16 cause torsion on sleeve 10, thereby reducing the cross section of sleeve 10 and increasing pressure applied to a penis inserted therein. Stored bulk torsional forces within sleeve 10 also provide a rotational force to return second housing element 16 to a neutral state, a force that may be augmented by spring element 20. Locking mechanism 22 may be used to maintain the position of the device (by opposing the return force(s) in varying rotational orientations and thereby a varying degrees of applied pressure. In a first mode a user may use the locking feature to permanently customize the device to provide a desired level of pressure during use. In a second mode a user may rotate the housings 14 and 16 and thereby vary the sensations dynamically during use.

General note: It is here understood that approximating the human body parts as idealized cylinders is an engineering approximation. The cavity 12 may be tapered, or have molded undulations, or irregularities and the like, and be well within the scope of this invention. In all cases, the topic at hand is the stimulation being applied to the human body, (i.e. relative changes in force and/or pressure) not the specific geometry of the contour of surface 5.

Figure 2:
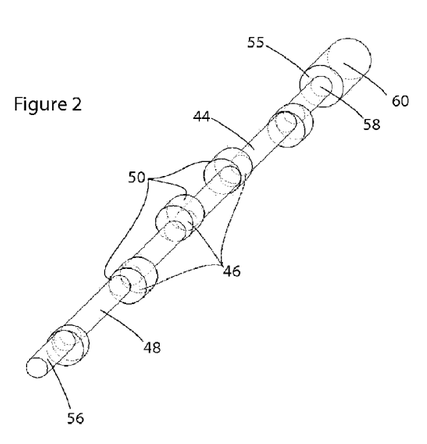
FIG. 2 is an isometric view of an internal rotary shaft for a sexual pleasure device.

FIG. 2 shows an embodiment in which rotary element 44 including at least one pressure element 46 are disposed intermittently along shaft 48, including first end 56 and second end 58. Pressure elements 46 are here shown as cylindrical elements offset with respect to shaft 48 in different directions, similar to the cam shaft of an internal combustion engine. Pressure elements 46 are disposed with pressure surfaces 50 located distal to shaft 48. Rotary elements 44 are driven by one or more motors 60 through any of a variety of known transmission means, the simplest of which is to place a motor at one end of each rotary element 44. Shaft 48 may be made of a flexible material, such as a coil spring or elastomeric equivalent if rotary element 44 used in a phallic-type device.

Figure 3:
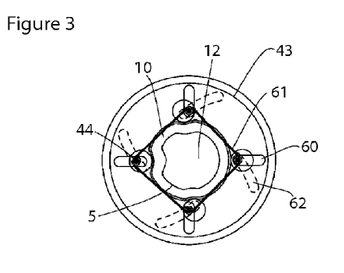
FIG. 3 is an end-wise cross sectional view of a device with multiple shafts as shown in FIG. 2.
Figure 4:
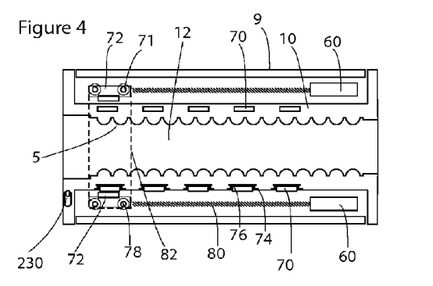
FIG. 4 is an axial sectional view of a sexual stimulation device incorporating magnets.

FIG. 3 shows an embodiment in which a plurality of rotary elements 44 are disposed along an approximately circular path around the circumference of sleeve 10. Low friction surface 43 is disposed around sleeve 10 and allows rotation of pressure elements 44 against sleeve 10 without causing undue abrasion. Low friction surface 43 may be provided by a thin Teflon sheet, or a lubricant either applied to the surface of the sleeve or incorporated in to the material of sleeve 10 itself. Referring now to FIGS. 3 and 4, a variety of sensations may be provided to a user at contact surface 5: In a first mode, rotary elements 44 are oriented such that the pressure elements 46 (and pressure surfaces 50) disposed in a common plane apply pressure to sleeve 10 at the same time. Therefore, as rotary elements 44 rotate in unison (through an encoder 55 or common transmission 61), a wave of constriction moves along the length of sleeve 10. In a second mode all rotary elements 44 are oriented in the same direction as each other, such that only one pressure surface 50 applies maximal pressure to sleeve 10 at a time, within a given plane. Therefore as rotary elements 44 rotate, a plurality of pressure waves traverse the length of sleeve 10 out of phase with each other, one wave for each rotary element 44. In a third mode rotary elements 44 are randomly oriented and or rotated with respect to one another, thereby producing random undulations along the perimeter of sleeve 10. In a fourth mode rotary elements 44 are driven alternately clockwise and anti clockwise, thereby providing a localized and varying pressure at any location along the length of sleeve 10. This location may be modified by rotating each of rotary elements 44 such that a different set of pressure elements 46 (within a plane) are nominally oriented toward sleeve 10. Pressure elements 46 may be nautilus shaped.

The position of first end 56 and second end 58 can vary radially to accommodate a variety of phallus diameters and/or to provide a varying degree of sensation according to the user's preference. In one embodiment first end 56 is constrained by both a radial channel 60 and slot 62. Slot 62 is a slanted or curved opening in disk 64 that constrains first end 56 to a defined radial displacement as a function of its rotation.

FIG. 4 shows an embodiment in which magnets 70, disposed on or near the outer surface of sleeve 10, are used to apply pressure along contact surface 5 to a penis located within sleeve 10, within housing 9. Magnets 70 may be co-molded within sleeve 10, as shown in the upper half of the figure, or adhered, as shown in the lower half of the figure. If adhered, it is desirable to use a carrier interface 74, preferably molded from a plastic, to both distribute the force of the magnet and to allow an intermediate bonding surface, i.e. magnet to plastic and plastic to sleeve 10. Carrier interface 74 also includes flange 76 to provide mechanical bonding. In one embodiment sensations are provided to a user by at least one drive magnet 72 brought into proximity to each fixed magnet 70 sequentially. Controls may be implemented with simple discrete electronics to drive in this embodiment a shuttle 78 is driven axially (as shown) by threaded shaft 80 driven by motor 60. Shuttle 78 may have sliding engagement with housing 9, or wheels 71. Other drive mechanisms, such a belt drive are within the scope of the invention. In one embodiment ring 82 holds a plurality of drive magnets 72 disposed around the circumference of sleeve 10 such that a single motor can displace the shuttle and provide a constricting sensation in a plurality of distinct locations simultaneously. (In such embodiments one of the motors 60 shown in the figure would be omitted.) another embodiment magnets 70 are replaced by a pressure element 46 is fashioned from a rolling element and located on shuttle 78. As is the case with other embodiments herein that include electronic operation, this embodiment may be operated remotely by phone or by the internet.

Figure 5:
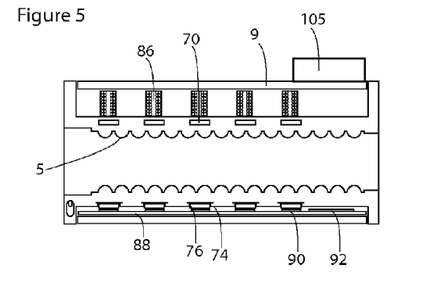
FIG. 5 is an axial sectional view of a sexual stimulation device incorporating magnets and electrically driven magnetic fields.

FIG. 5 shows an embodiment that uses the sleeve 10 and magnet 70 assembly described in FIG. 4, but provides actuation by means of a series of conductive coils 90 and/or solenoids 86, as shown on the upper half of the figure, or printed within a printed circuit board 88, as shown on the lower half of the figure. Coils 90 are in electrical communication with a control system 92 and a power source 105 such that one or more magnets 70 may be displaced individually or in sets to provide a wide variety of sensory outputs to a penis located within sleeve 10. A partial list of the variety is provided in FIG. 2, however this embodiment may also actuate individual (i.e. specific) locations, as opposed to rings or lines, or relatively large areas, and may provide differing frequencies of stimulation at each coil 90. For example, while all actuators provide a constant force (i.e. pure contracture) rhythmically altering force, or a force altering in sequence of waves along sleeve 10, one or more coils 90 may provide a low or high frequency localized vibration, which may remain in one location, or may be superimposed onto the aforementioned output. The system may provide random (or pseudo-random) output, thereby massaging/tingling sensation to the body part over a range of frequencies, from very low (e.g. zero) to very high (e.g. 1000 Hertz). Including a sensor 230 (such as infrared or capacitive) to measure the presence and/or displacement of the penis within the device.

Figure 6:
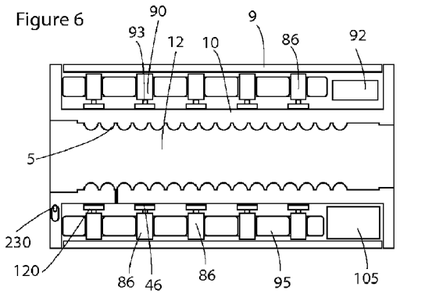
FIG. 6 is an axial sectional view of a sexual stimulation device incorporating solenoids.

FIG. 6 shows embodiment with similar functionality described in FIG. 5. In this embodiment, the force is applied to sleeve 10 by a mechanical displacement of a post 93 within coil 90, together forming solenoid 86. Solenoids 86 are restrained to an approximately orthogonal orientation by form 95 and capped by pressure elements 46. Alternately solenoids 86 may be capped by weights 120. Ones of solenoids 86 may be disposed at an angle, thereby providing a stretching in sleeve 10, thereby enhanced friction and sensation on the user.

Figure 7:
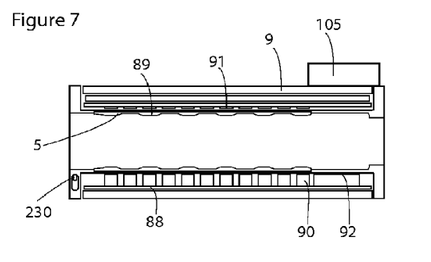
FIG. 7 is an axial sectional view of a sexual stimulation device incorporating ferrofluids.

FIG. 7 shows an embodiment with similar base functionality described in FIG. 5, although enhanced to provide a more continuously variable output. The regions of displacement are more continuously variable, providing more subtle variations. In this embodiment, the force is applied to sleeve 10 by ferrofluids (such as magnatite or hematite coated which may be coated with surfactant such as a soy lecithan or oleic acid) encased in a sealed bag 89 and under the influence of fields imposed by coils 90 and/or electrodes 91.

Figure 8:
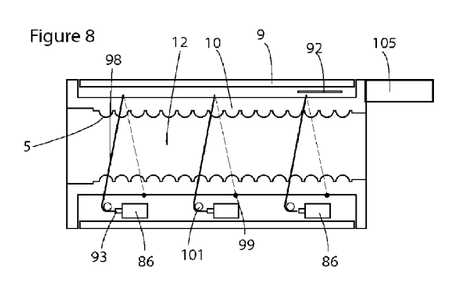
FIG. 8 is an axial sectional view of a sexual stimulation device incorporating passive tension elements.

FIG. 8 shows an embodiment in which sleeve 10 is constricted in at least one location along the major axis by a tensile member 98 disposed around at least a portion of the circumference of sleeve 10 at least at one cross section. Tensile member 98 is constrained by anchor point 99 at one and held by the post 93 of solenoid 86, which serves as the actuator. In the embodiment shown, the orientation of the tension is redirected by pulley wheel element 101 (or low friction slide, or equivalent). The result, as the embodiments of FIGS. 8-11 is a repeatable and local reduction of the cross sectional area of cavity 12. Control system 92 enables one or more regions of sleeve 10 to undergo simultaneous, local and/or wavelike constrictions at contact surface 5. Other actuators, such as rotary motors can be used.

Figure 9:
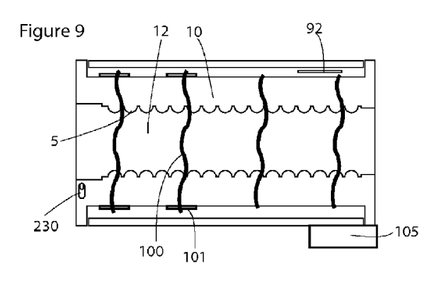
FIG. 9 is an axial sectional view of a sexual stimulation device incorporating shape memory alloy.

FIG. 9 shows an embodiment in which the tensile member 98, solenoid 86 and the associated mechanics of FIG. 8 are replaced by a shape memory element 100 such as copper-zinc-aluminum-nickel, copper-aluminum-nickel, and nickel-titanium (NiTi) alloys. Control system 92 directs current flowing through each element 100 causes heating and expansion of memory element 100, which in turn reduces the constriction upon sleeve 10. Reducing or stopping the current flow allows memory elements 100 to return to a neutral and constricted state, thereby reducing the cross section of cavity 12. One advantage is silent operation. Pads 101 are made of a thermally conductive material such as aluminum and serve to decrease the cooling time of memory elements 100 and also to distribute the load applied to sleeve 10.

Figure 10:
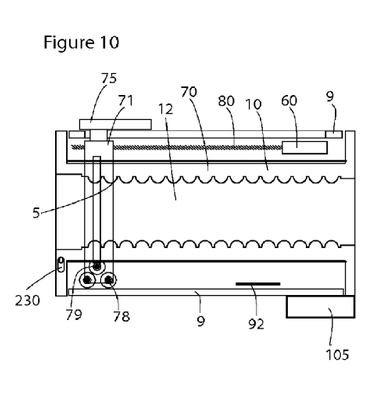
FIG. 10 is an axial sectional view of a sexual stimulation device incorporating a mechanically driven stimulation zone.

FIG. 10 shows a embodiment in which the magnets 70 of FIG. 4 are replaced by a rolling constriction element 79 disposed on shuttle 78 that applies a force to sleeve 10, and thereby any penis located within at contact surface 5. Shuttle 78 may be displaced axially along sleeve 10 through displacement actuator 80 and motor 60, which may be controlled by the user via controls 92. Shuttle 78 may also be displaced axially along sleeve 10 with handle 75, which protrudes through housing 9.

Figure 11:
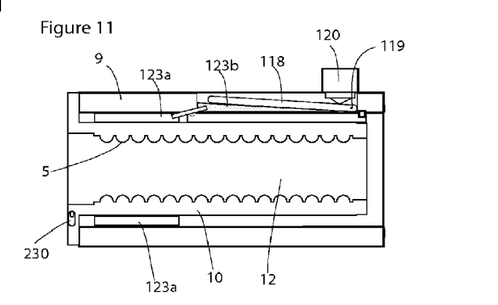
FIG. 11 is a sectional view of an artificial vagina with a fluidic contraction.

FIG. 11 shows an embodiment in which a first part of fluid filled bag 123a is predominantly surrounding at least a portion of sleeve 10 and constrained on its other side by a portion of housing 9. A second part of fluid filled bag 123b is disposed beneath pressure plate 118 that rotates about pivot 119. Actuator element 120, here shown as a sliding knob in a neutral position closest to pivot 119, applies force to pressure plate 118 and thereby pressurizes second part of fluid filled bag 123b (as shown here when the sliding knob is displaced to the left). The fluid within the second part of the fluid filled bag 123b then flows into first part of fluid filled bag 123a, and applies a constriction to sleeve 10. In some constructions the first and second parts of the bag (123a and 123b) may be co-located.

Figure 12A:
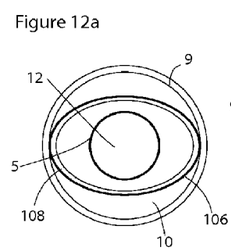
FIGS. 12a and 12b are end-wise sectional views showing rotary constriction of a sexual stimulation device.
Figure 12B:
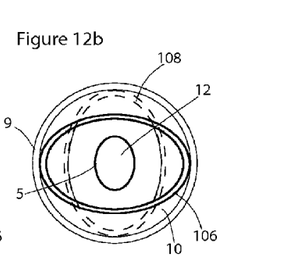

FIG. 12a shows an embodiment in which sleeve 10 inside housing 9. Sleeve 10 is constrained by first contour 106 and second contour 108, which cannot be seen in this figure because it is aligned with first contour 106. Regions of first contours 106 and second contours 108 alternate along at least a portion of the axis of sleeve 10, like interlaced fingers, simultaneously supporting sleeve 10 and allowing the other contour to also interact with sleeve 10 by application of additional force at the same time. In this figure cavity 12 is shown in a neutral state. In FIG. 12b, the second contour 108 has been rotated (manually or under electrical power) to be oriented at a 90 degree angle from first contour 106. Sleeve 10 is constricted by simultaneous pressure from the two contours, and cavity 12 is thereby in a constricted state, and subsequently applying an additional constrictive force to any penis located within at contact surface 5. This is an example of an embodiment in which the user may vary the performance of the device without adjusting grip on the device.

Figure 13A:
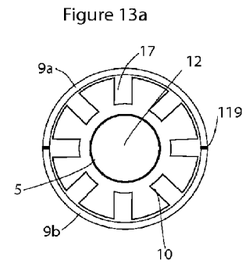
FIGS. 13a and 13b are end-wise sectional views showing linear constriction of a sexual stimulation device.
Figure 13B:
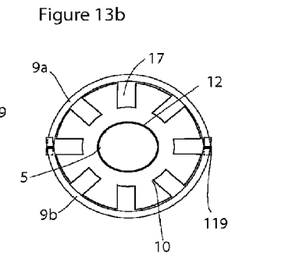

FIG. 13a shows an embodiment in which housing 9 split to include two portions, upper housing 9a and lower housing 9b, together enclosing sleeve 10 without compressing it, placing cavity 12 in a neutral state. In this embodiment, housings 9a and 9b are rotatably connected by pivot 119. In another embodiment the housings are interlocking and in a third they mechanically engage with sleeve 10. FIG. 13b shows upper housing 9a and lower housing 9b displaced toward one another (manually or under electrical power) and thereby constricting sleeve 10, applying a bulk pressure that places cavity 12 in a constricted state, and subsequently applies a constrictive force to any penis located within. Voids 17 decreases the force required to impose a specific constricted state. This is an example of an embodiment in which the user may vary the performance of the device without adjusting grip on the device.

Figure 14A:
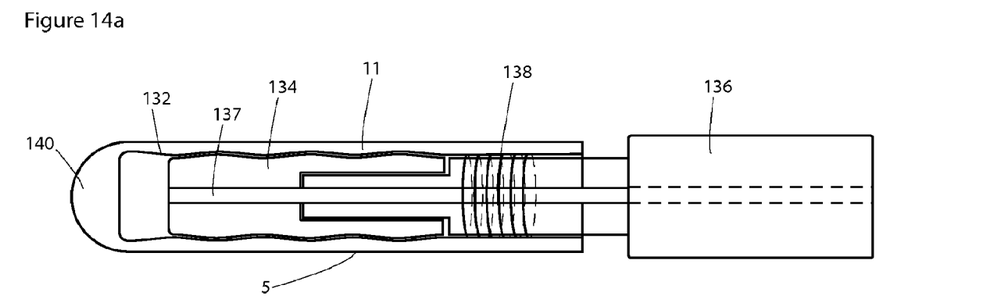
FIGS. 14a and 14b are sectional views of a dildo with two shape states, mechanically induced.
Figure 14B:
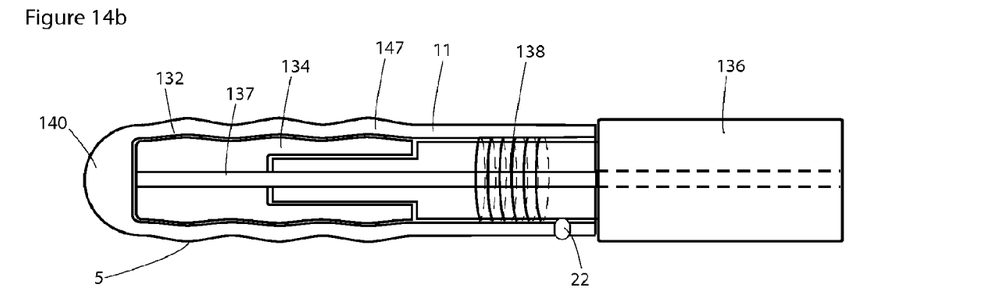

FIG. 14a shows an embodiment in which sheath 11 formed of an low-durometer elastomeric material, such as silicon, including undulating features 132 on the interior. Core element 134 is made of a more rigid material, such as polyurethane (Shore A 65), and is slidingly engaged within sheath 11. Core element 134 is mounted to handle 136. Vent 136 traverses the length of sheath 11 allowing air located near the distal end 140 to escape as the device is activated to the state shown in FIG. 14b. In FIG. 14b the core element 134 is displaced relative to sheath 11 and thereby altered the shape of the exterior of sheath 11. Spring element 138 provides a force roughly equivalent to the force required to flex sheath 11, thereby reducing the force needed to activate the device. By selecting the force level of spring element 138 at manufacture or by allowing the user to adjust the force applied by spring element 138, the device may have three modes. In mode 1 the device is biased to have more surface texture upon motion toward distal end 140. In mode 2 the devices is biased to have more surface texture upon motion away from distal end 140. In mode 3, the device is nearly bi-stable and will readily change shape in either direction. Locking mechanism 22 may be used to maintain the position of the device (by opposing the return force(s) in varying rotational orientations and thereby a varying degrees of applied pressure.

Figure 15A:
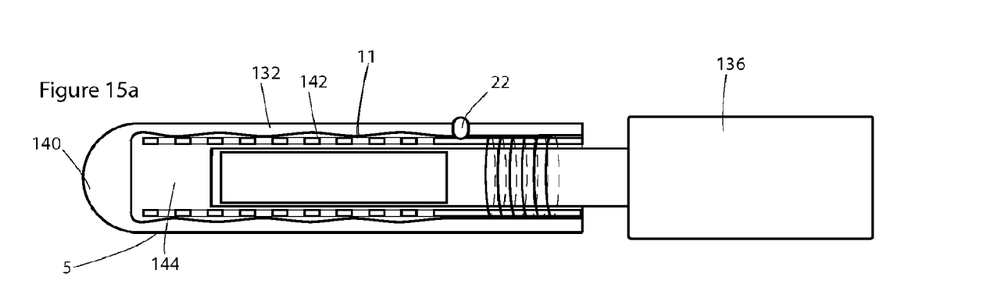
FIGS. 15a and 15b are sectional views of a dildo with two shape states, fluidically induced.
Figure 15B:
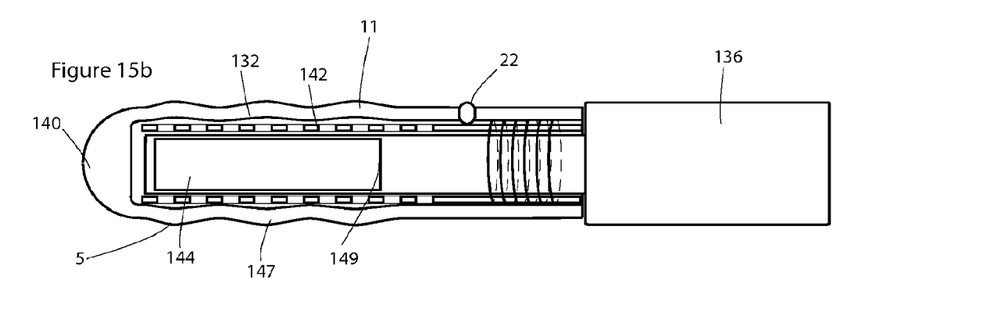

FIG. 15a shows an embodiment in which sheath 11 formed of an low-durometer elastomeric material, such as silicon, including undulating features 132. Body 142 provides rigidity to sheath 11 and provides an internal channel 144 into which handle 136 may slide. Piston surface 149 is disposed on body 142 and serves to pressurize internal channel 144 when handle 136 is pressed into sheath 11. Body 142 is perforated, allowing fluid to transfer from the internal channel 44 outwards, thereby altering the shape of the exterior of sheath 11. FIG. 15b shows the device in an activated state, with added surface texture 147. Locking mechanism 22 may be used to maintain the position of the device (by opposing the return force(s) in varying rotational orientations and thereby a varying degrees of applied pressure.

Figure 16A:
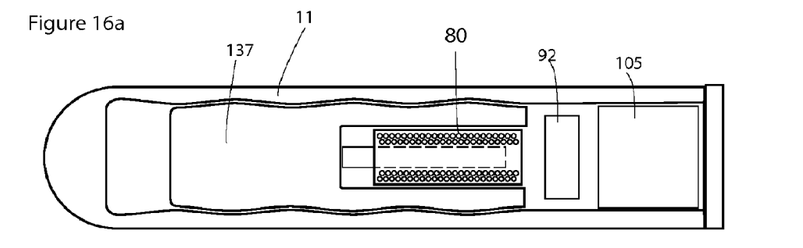
FIGS. 16a and 16b are sectional views of a dildo with two shape states, electromechanically induced.
Figure 16B:
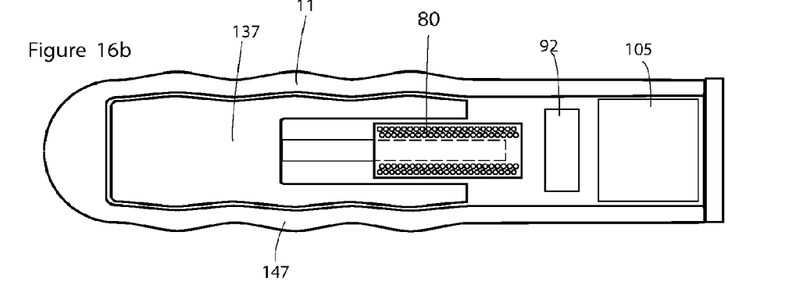

FIG. 16a is the same as FIG. 14a, except the spring element 138 has been replaced by linear displacement actuator 80. FIG. 16b is the same as FIG. 14b, except the spring element 138 has been replaced by displacement actuator 80. Linear displacement actuators 80 include two types: the first is solenoids 86, typically a metal core within a coil of wire (E.G. with a return spring) typically used for transient force application with a low degree of control; the second is a linear motor 87, typically a magnet placed within a magnetic field and typically used for higher degrees of control. As a result, the transition between the two figures occurs electronically and can be performed by a remotely located person telephonically, or by the internet.

Figure 17:
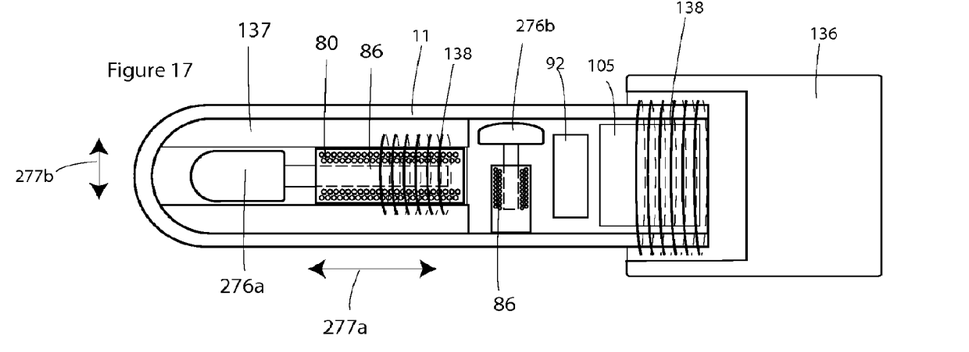
FIG. 17 are sectional views of a dildo with a large mass, large stroke, linear actuators.

FIG. 17 shows a sexual pleasure device with a linear displacement actuator 80 oriented radially, and accelerating a mass 276b and a second linear displacement actuator 80 oriented axially, and accelerating a mass 276a within the body 137 of the device. The weight of mass 276 is selected according the desired performance dictated by MV=mv where:

m=mass of Mass 276
v=the velocity imposed by displacement actuator 80
M=the mass of the device, less m
V=the velocity of the device as it physically displaces along the axis of motion.

This is different than the vibration motors 152 currently built into vibrator products. Vendors today manufacture vibrators with a small mass (typically under 5 grams), with high frequency (typically 200 to 1000 RPM) and with the mass located off-center on a rotary motor. There are also phallus-shaped devices with externally motor driven operation. In the instant invention, the mass is substantially increased, the frequency is substantially decreased, the motion is linear and the drive mechanism is internal. The objective is to provide a sensation that is not vibratory, but rather a displacement of the device which is a subtle enhancement of self-directed hand motion. Unlike the prior art, this embodiment is capable of a single cycle providing a significant sensation to a user, as a degree of motions and hence friction is felt, as opposed to merely non-motile vibration. This additional motion may be along the major axis, as provided by mass 276b and its associated linear displacement actuator 80, or may be along the a radial axis, as provided by mass 276b and its associated linear displacement actuator 80. The user's hand is shielded from the motions of the device through an isolation mechanism such as spring element 138 disposed between handle 136 and body 137. The device can vary the amplitude and acceleration curves as well as the frequency, thereby enabling a wide range of sensations to the user. For example, one embodiment provides multiple sequential stimuli in a single direction. By way of explanation, let us assume an overall travel distance of the linear displacement actuator 80 is 27 mm. The device could therefore provide three sequential 9 mm "thumps", all in a first direction without recoiling. In one embodiment the controller 92 can provide a plurality of such sequential unidirectional fast "thumps" in a relatively short time before recoiling to the origin at a significantly slower rate and/or decelerating such that the recoil is NOT detected by the user, and then repeats the unidirectional motion, again in the first direction. By modifying the acceleration curves, displacements and sequences, a wide range of novel sensations may be provided.

Figure 18:
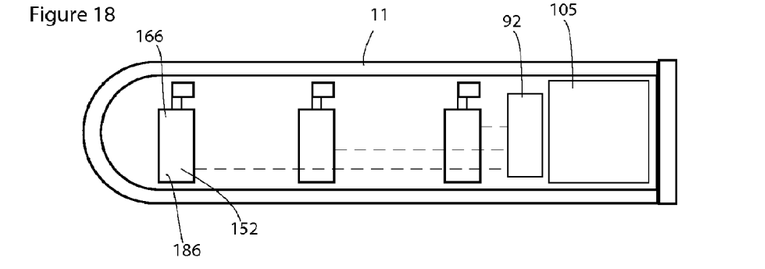
FIG. 18 are sectional views of a dildo with a control system for independent control of vibrator motors.

FIG. 18 shows a device for sexual stimulation including a plurality of actuators 166 (including electromechanical devices such as solenoids 86 and vibratory motors 152) and a controller capable of activating and deactivating each vibratory element 152 independently and without human intervention. This architecture enables a variety of embodiments. In one embodiment, each motor is activated sequentially such that each actuator 166 is on for a brief period, thereby providing a "large-scale" wave-like progressive sensation, despite the absence of large scale wave. Here "large-scale" is used to differentiate between the small-scale waves that emanate from each vibratory motor independently. The result is a low cost means to provide a high degree of sensation variation.

Figures 19, 20:
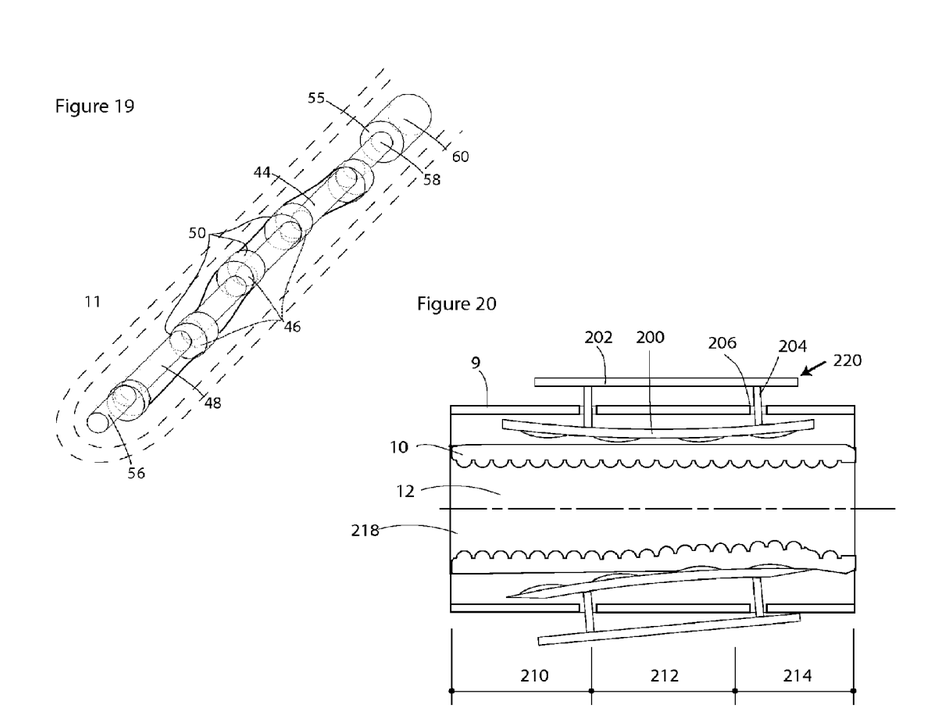
FIG. 19 is a schematic of input to the control system.
FIG. 20 shows an axial sectional view of a sexual stimulation device with pressure plate sensations.

FIG. 19 shows a telephonic network 170 and/or the internet 172 and/or arousal sensors 174 used as inputs to control and or augment the control imposed by control system 92. This applies to any Figures here shown to include a control system 92. The addition of arousal sensors 174 may enhance the experience, as disclosed in the inventor's co-pending application 20030073881, incorporated here by reference.

FIG. 20 shows housing 9, made of a rigid material such as ABS encasing sleeve 10 made of a low durometer elastomer such as styrene-ethylene propylene-styrene block copolymer (SEPS) or other material that simulates human flesh. It is known in the art that a suitable elastomeric gel may be formed from a mixture of plasticizing oil and a block copolymer comprising an admixture of a styrene ethylene butylene styrene block copolymer and a styrene ethylene propylene styrene block copolymer. Cavity 12 is molded to accommodate a human penis. For descriptive purposes it is useful to define three regions: proximal region 210 which includes an opening 218 designed to insert a penis, distal region 214 located at the deepest end of cavity 12 and a central region 212. Pressure plate 200 is disposed between housing 9 and sleeve 10. In one embodiment (shown) pressure plate 200 extends parallel with the major axis of the sleeve 10. In one embodiment (not shown) pressure plate 200 may be implemented in one or more discrete locations, allowing a plurality of independent pressure points along one edge of sleeve 10. Control surface 202 is connected to pressure plate 200 by stanchions 204 that protrude through openings 206. Pressure plate 200 is shown curved, however other shapes are possible, such as the flat contour shown in FIG. 21, and may further include protrusions 216 (or voids). In the embodiment shown, the device has two such independently operable mechanisms 220 (i.e. mechanism 220=200, 202, 204, 206, in combination) each disposed to contact sleeve 10 along one lateral edge although any number of mechanisms may be implemented. The mechanisms may be coupled to operate dependently as indicated elsewhere in this document. By pressing the control surface 202 of each mechanism the user imposes a pressure to the surface of the sleeve material at a specific location along the length of sleeve 10. When a penis is inserted at the specific location prior to activation this will be perceived as a localized pressure at that specific location and concentrated on the side of the sleeve 10 on which the mechanism 220 is located. The lower durometer of the sleeve material assures that the pressure and volume changes will be confined locally, to the side of the device at which the mechanism 220 is located, and to the length along the sleeve 10. When the volume is reduced prior to introduction of the penis at the specific location, this will be perceived as a reduction of the cross sectional area (i.e. volume) at that specific location, with the volume reduction concentrated on the side of the sleeve 12 on which the mechanism 220 is located. The upper half of the figure shows the device in a non-activated state. The lower half shows mechanism 220 locally reducing the volume of cavity 12 in the distal region 214. The users has complete control of the force level, timing and location of the localized volume reductions thereby providing a dynamically customizable sensation along the length of the cavity, including the ability to simulate vaginal constrictions by operating opposing mechanisms 220 at the same time. Furthermore, because the control surfaces mimic the gripping surface of the housing 9, the user may simultaneously hold the device while activating it. Locking mechanism 232 provides means to offset pressure plate 200 to a desired preset, thereby altering the volume range of cavity 12. In one embodiment, the actuation may be implemented by electromagnetic means, as elsewhere in this filing.

Four operational examples:

The user may apply force near central region 212 to displace pressure plate 200 without rotation and thereby apply pressure on sleeve 10 in the center region 212, causing a pressure within the material of sleeve 10 and a local reduction of the volume of cavity 12 in the center region 212.

The user may apply force near proximal region 210 to displace pressure plate 200 with (or potentially without) rotation and thereby apply pressure on sleeve 10 in the proximal region 210, causing a pressure within the material of sleeve 10 and a local reduction of the volume of cavity 12 in the proximal region 210.

The user may apply force near distal region 214 to displace pressure plate 200 with rotation (or potentially without) and thereby apply pressure on sleeve 10 in the distal region 214, causing a pressure within the material of sleeve 10 and a local reduction of the volume of cavity 12 in the distal region 214.

The user may apply force uniformly across multiple regions at once and thereby apply pressure on sleeve 10 along its length, causing a generalized reduction of the volume of cavity 12.

The device therefore provides the user dynamic, interactive and spontaneous control: the ability to vary the degree of force applied along the length of control surface 202 and thereby provide a range of sensations under interactive user control, including the degree of force, location, and timing of localized volume reduction. Furthermore, this functionality is provided concurrent with, and integral to, the action of grasping the device. The variable sensation is independent of any thrusting motion. The same sensations are provided at different locations within the device at different times. The device provides a contractile sensation that can, by the user's input, provide an undulating contractile output. The device provides a localized output sensation at a different location at which the control is input. In this embodiment, as with some others in the application, the device may provide a variety of sensations without relative motion between the sexual organ and the device.

Figure 21:
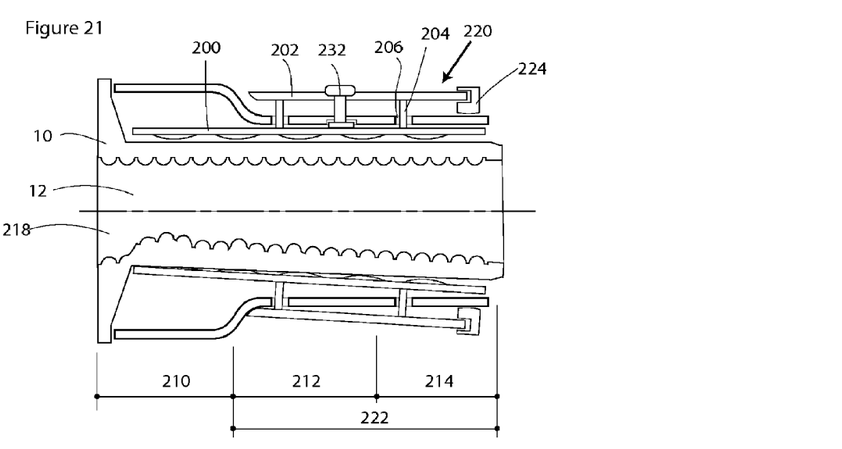
FIG. 21 shows an axial sectional view of a sexual stimulation device with pressure plate sensations provided in a region different than the input region.

FIG. 21 shows an embodiment in which the cross sectional area of proximal region 210 is significantly larger than the cross sectional area of the combined region 222. The upper half of the figure shows the device in a non-activated state. The lower half shows mechanism 220 locally reducing the volume of cavity 12 in the proximal region 210. In cylindrical embodiments, such as intended in this figure, the diameter of proximal region 210 is significantly larger than the diameter of combined region 222. In this embodiment, pressure plate 200 is disposed in combined region 222, while pressure plate 200 extends into proximal region 210, enabling the user to apply force in a first region and implement a volume reduction in the cavity 12 of a second region. For example, force applied near central region 212 or distal region 214, displaces pressure plate 200 to apply pressure on sleeve 10 in the proximal region 210, causing a pressure within the material of sleeve 10 and a local reduction of the volume of cavity 12 in the proximal region 210. There is psychological and experiential benefit to providing stimulus in a different region to where the user's hand is located. One embodiment includes a pivot point 224, shown located at the distal end of control surface 202 and disposed to provide a fulcrum about which mechanism 220 may rotate, as shown in the lower half of the figure. Pivot point 224 may be co-molded with control surface 202, pressure plate 200, or it may be independently molded and therefore detachable. The functionality described may be additive to the functionality described in FIG. 20. Volume reductions to the cavity 12 may be maintained with displacement locks 232.

Some embodiments, such as described in FIGS. 2, 4, 5, 6, and 7, may also be adapted for use in phallic-type (dildo) devices. The reader may see an example of the adaptation by treating the upper or lower half of FIGS. 4-7 as half of the cross section of a dildo in which the mechanics are disposed within a sheath 11 rather than outside a sleeve 10.

The details of one or more embodiments of the invention are set forth in the accompanying drawings and descriptions. While several embodiments have been described, it will be apparent to one skilled in the art how the form, structure and arrangement of these embodiments may be varied (or combined with each other) and yet remain within the scope of the instant invention. The scope of the invention shall therefore be defined by the claims that follow.

What is claimed is:

1. A sexual pleasure device comprising:
an elastomeric sleeve including an elongated cavity;
a rigid housing at least partially surrounding the elastomeric sleeve; and
a pressure element disposed proximal to an inner surface of the rigid housing and distal to and operably engaged with the elastomeric sleeve; and
an actuator disposed distal to the rigid housing and connected to the pressure element,
wherein the actuator is operable to control movements of the pressure element, relative to the housing, thereby to apply pressure to the elastomeric sleeve.

2. The sexual pleasure device of claim 1, wherein the elongated cavity is configured to simulate a vagina.

3. The sexual pleasure device of claim 1, wherein the rigid housing is approximately cylindrical.

4. The sexual pleasure device of claim 1, wherein the pressure element is disposed in a discrete region, and wherein the actuator is operable to displace the pressure element, thereby to impose a localized pressure on the elastomeric sleeve.

5. The sexual pleasure device of claim 1, wherein the actuator is operable to control movements of the pressure element, relative to the housing, thereby to adjust a volume of the elongated cavity.

6. The sexual pleasure device of claim 1, wherein the actuator is operable to affect a reduction in the volume of the elongated cavity only in a region proximate the pressure element.

7. The sexual pleasure device of claim 1, wherein the actuator is operable to affect a reduction in the volume of the elongated cavity localized to one side of the cavity.

8. The sexual pleasure device of claim 1, wherein displacement of the actuator, relative to the rigid housing, within a first region along a length of the elongated cavity effects a reduction in the volume of the elongated cavity in a second region, along the length of the elongated cavity.

9. The sexual pleasure device of claim 1, further comprising a pivot point about which the pressure element can move.

10. The sexual pleasure device of claim 1, wherein the pivot point is removable.

11. The sexual pleasure device of claim 1,
wherein the elastomeric sleeve includes an opening arranged to accommodate insertion of a male sex organ into the elongated cavity,
wherein the rigid housing comprises:
a first region, along a length of the rigid housing, arranged proximate to the opening; and a second region, along the length of the rigid housing, associated with a majority of the length rigid housing, and wherein a cross-sectional area of the first region is larger than a cross-sectional area of the second region.

12. The sexual pleasure device of claim 11, wherein the actuator defines a control surface, and wherein the control surface is disposed predominately within the second region along a length of the rigid housing.

13. The sexual pleasure device of claim 1, wherein the elastomeric sleeve comprises an elastomeric gel formed from a mixture of plasticizing oil and a block copolymer, the block copolymer comprising an admixture of (i) a styrene ethylene butylene styrene block copolymer and (ii) a styrene ethylene propylene styrene block copolymer combined in a ratio of approximately 1:4 to 4:1.

14. The sexual pleasure device of claim 1, wherein the rigid housing includes a grasping region arranged to be grasped by a user for manipulation of the device, and wherein the actuator is disposed within the grasping region.

15. The device of claim 1 wherein the actuator is a manually operable handle.

16. The device of claim 1 further including at least one stanchion disposed between the actuator and the pressure element.

17. The device of claim 16 further including a hole in the rigid housing through which passes said at least one stanchion.

18. The device of claim 1 wherein the pressure element may rotate relative to the housing.

19. A method for providing sexual pleasure, the method comprising: inserting a male sex organ into a cavity of an elastomeric sleeve, the elastomeric sleeve being at least partially surrounded by a rigid housing engaging an actuator disposed distal to the rigid housing and exposed to manual contact to effect movement of a pressure element disposed proximal to the rigid housing and distal to and operably engaged with the elastomeric sleeve, thereby modifying a sensation perceived by the male sex organ.

20. The method of claim 19, wherein engaging the actuator comprises applying a first force to the actuator, and wherein the first force is applied within a first region along a length of the cavity and a resulting increase in pressure is applied to the male sex organ within a second region, at a distance from the first region, along the length of the cavity.

21. The method of claim 19, further comprising dynamically controlling the sensation perceived by the male sex organ as a function of time.

22. The method of claim 21 wherein the dynamically controlled sensation is modified contemporaneously at the manual command of the user.

23. The method of claim 19, further comprising dynamically controlling the sensation perceived by the male sex organ selectively as a function of location along a length of the elastomeric sleeve.

24. The method of claim 23 wherein the dynamically controlled sensation is modified contemporaneously at the command of the user.

25. The method of claim 19, further comprising dynamically controlling the sensation perceived by the male sex organ as a function of force applied to the actuator.

26. The method of claim 25 wherein the dynamically controlled sensation is modified manually.

27. The method of claim 19, wherein modifying the sensation comprises increasing a pressure applied to the male sex organ via the elastomeric sleeve at a location proximal to the pressure element.

28. The method of claim 19, wherein a plurality of sensations may be provided in the absence of linear displacement between the sex organ and the cavity.

* * * * *